United States Patent
Ng et al.

(10) Patent No.: US 12,076,432 B2
(45) Date of Patent: Sep. 3, 2024

(54) METHOD OF REPAIRING OXIDATIVELY TREATED HAIR

(71) Applicant: Conopco, Inc., Englewood Cliffs, NJ (US)

(72) Inventors: Andrew Ng, Wirral (GB); Prem Kumar Cheyalazhagan Paul, Wirral (GB); Charlotte Breony Tandy Rogers, Kingswood (GB)

(73) Assignee: Conopco, Inc., Englewood Cliffs, NJ (US)

( * ) Notice: Subject to any disclaimer, the term of this patent is extended or adjusted under 35 U.S.C. 154(b) by 909 days.

(21) Appl. No.: 17/051,233

(22) PCT Filed: Apr. 25, 2019

(86) PCT No.: PCT/EP2019/060684
§ 371 (c)(1),
(2) Date: Oct. 28, 2020

(87) PCT Pub. No.: WO2019/214965
PCT Pub. Date: Nov. 14, 2019

(65) Prior Publication Data
US 2021/0236402 A1    Aug. 5, 2021

(30) Foreign Application Priority Data
May 10, 2018   (EP) .................................... 18171692

(51) Int. Cl.
| | | |
|---|---|---|
| *A61K 8/44* | (2006.01) | |
| *A45D 19/00* | (2006.01) | |
| *A61K 8/49* | (2006.01) | |
| *A61Q 5/00* | (2006.01) | |
| *A61Q 5/12* | (2006.01) | |

(52) U.S. Cl.
CPC ............. *A61K 8/44* (2013.01); *A45D 19/005* (2021.01); *A61K 8/447* (2013.01); *A61K 8/4913* (2013.01); *A61K 8/492* (2013.01); *A61K 8/4946* (2013.01); *A61Q 5/002* (2013.01); *A61Q 5/12* (2013.01)

(58) Field of Classification Search
CPC ......... A45D 19/005; A61Q 5/002; A61Q 5/12
See application file for complete search history.

(56) References Cited

U.S. PATENT DOCUMENTS

2019/0160001 A1*   5/2019   Kang .................. A61K 8/8105

FOREIGN PATENT DOCUMENTS

| CN | 1336817 | 2/2002 |
|---|---|---|
| EP | 0415596 | 3/1991 |
| EP | 0415598 | 3/1991 |
| JP | 2002534369 | 10/2002 |
| JP | 2006282532 | 10/2006 |
| JP | 2016190806 | 3/2019 |
| WO | WO0040217 | 7/2000 |
| WO | WO2018146051 | 8/2018 |
| WO | WO2018146054 | 8/2018 |

OTHER PUBLICATIONS

Search Report and Written Opinion in EP18171693; dated Oct. 19, 2018.
Search Report and Written Opinion in EP18171692; dated Oct. 19, 2018.
Search Report and Written Opinion in PCTEP2019060684; dated Jul. 22, 2019.

* cited by examiner

*Primary Examiner* — Andrew S Rosenthal
(74) *Attorney, Agent, or Firm* — Foley & Lardner LLP

(57) ABSTRACT

A method of repairing oxidatively-treated hair, the methods comprising the sequential steps of: (i) soaking hair in an aqueous treatment composition, (ii) rinsing the hair of step (i); characterised in that the aqueous treatment composition comprises 0.1 to 6 wt % N-acetyl amino acid, based on the total weight of the composition, wherein the N-acetyl amino acid is selected from the group consisting of N-acetyl glycine, N-acetyl alanine, N-acetyl proline, N-acetyl leucine, N-acetyl isoleucine, N-acetyl valine, N-acetyl tyrosine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof, gives damage repair benefits.

20 Claims, No Drawings

METHOD OF REPAIRING OXIDATIVELY TREATED HAIR

CROSS-REFERENCE TO RELATED APPLICATIONS

This application is a U.S. National Stage Application under 35 U.S.C. § 371 of International Application No. PCT/EP2019/060684, filed on Apr. 25, 2019, which claims the benefit of European Patent Application No. 18171692.9, filed May 10, 2018, the entire disclosures of which are hereby incorporated by reference for any and all purposes.

FIELD OF THE INVENTION

This invention relates to a method for repairing oxidatively-treated hair with a composition comprising an N-acetyl amino acid.

BACKGROUND OF THE INVENTION

The purpose of bleaching is to eliminate or lighten the natural hair colour by the reaction of an oxidizing agent with the melanin pigment. Examples of oxidizing agents that can be used are hydrogen peroxide, potassium, sodium or ammonium salts of perborate, percarbonate, persulfate and percarbamide, and mixtures thereof. Bleaches are also used during oxidative dyeing treatments. Oxidative (or "permanent") dye compositions comprise "precursor dyes" which are small molecules capable of diffusing into the hair. These molecules mainly belong to three classes of aromatic compounds: diamines, aminophenols and phenols. They are sufficiently small to diffuse in the hair shaft where, once activated by an oxidizing agent such as hydrogen peroxide, they further react with other precursors to form larger coloured complexes.

Oxidative treatments of hair are very popular with consumers since they provide good results which are relatively unaffected by light, shampooing and perspiration. However, the process is not without drawbacks. Repeated oxidative treatments over prolonged periods may damage or weaken hair, making it prone to breakage and reduced lustre.

WO00/40217 broadly discloses compositions containing N-acetyl amino acids for use to improve cosmetic and dermatological disorders, including changes and damage to skin nail and hair associated with ageing as well changes or extrinsic factors such as sunlight, radiation, air pollution, wind, cold, heat, dampness, chemicals, smoke and cigarette smoking. An aqueous solution of N-acetyl composition may be mixed with a shampoo base and an example discloses a shampoo composition (for hair, scalp or body wash) that contains 4% N-acetyl-L-arginine.

Our co-pending application, PCT/EP2018/052826, discloses a method having a first step that requires washing oxidatively treated hair, followed by two further steps involving soaking the hair in a composition comprising N-acetyl glycine and then drying the soaked hair. Damage associated with oxidative treatment of hair is alleviated as a result.

Our second co-pending application, PCT/EP2018/052825, also discloses a method involving washing hair, followed by soaking the hair in a composition comprising at least 1 wt % of N-acetyl lysine and then drying the soaked hair. The strength of the hair fibres is enhanced.

SUMMARY OF THE INVENTION

The present invention provides a method of repairing oxidatively-treated hair, the method comprising the sequential steps of:

(i) soaking hair in an aqueous treatment composition,
(ii) rinsing the hair of step (i);
characterised in that the aqueous treatment composition comprises 0.1 to 6 wt % N-acetyl amino acid, based on the total weight of the composition, wherein the N-acetyl amino acid is selected from the group consisting of N-acetyl glycine, N-acetyl alanine, N-acetyl proline, N-acetyl leucine, N-acetyl isoleucine, N-acetyl valine, N-acetyl tyrosine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

The method may further comprise a washing step, sequential to step (ii), as follows:

(i) soaking hair in an aqueous treatment composition,
(ii) rinsing the hair of step (i);
(iii) washing the hair of step (ii);
characterised in that the aqueous treatment composition comprises 0.1 to 6 wt % N-acetyl amino acid, based on the total weight of the composition, wherein the N-acetyl amino acid is selected from the group consisting of N-acetyl glycine, N-acetyl alanine, N-acetyl proline, N-acetyl leucine, N-acetyl isoleucine, N-acetyl valine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

DETAILED DESCRIPTION AND PREFERRED EMBODIMENTS

All molecular weights as used herein are weight average molecular weights, unless otherwise specified.

The Aqueous Treatment Composition

The aqueous treatment composition for use in the method of the invention preferably comprises an aqueous continuous phase.

By "aqueous continuous phase" is meant a continuous phase which has water as its basis. Accordingly, the aqueous treatment composition will generally comprise at least 60%, preferably at least 70% and more preferably at least 80% water (by weight based on the total weight of the composition). Preferably, the composition comprises no more than 99% and more preferably no more than 98% water (by weight based on the total weight of the composition). Other organic solvents may also be present, such as lower alkyl alcohols and polyhydric alcohols. Examples of lower alkyl alcohols include $C_1$ to $C_6$ monohydric alcohols such as ethanol and isopropanol. Examples of polyhydric alcohols include propylene glycol, hexylene glycol, glycerin, and propanediol. Mixtures of any of the above described organic solvents may also be used.

The N-Acetyl Amino Acid

The aqueous treatment composition for use in the method of the invention comprises N-acetyl amino acid.

The N-acetyl amino acid may be classified according to the equivalent amino acid sidechains and may be selected from the group consisting of i) N-acetyl hydrophobic uncharged aliphatic amino acids, ii) N-acetyl hydrophobic uncharged aromatic amino acids, iii) N-acetyl polar uncharged amino acids, iv) N-acetyl positively charged amino acids, v) N-acetyl negatively charged amino acids and mixtures thereof.

Hydrophobic uncharged aliphatic amino acids are selected from glycine, alanine, proline, leucine, isoleucine, valine and mixtures thereof.

In the method of the invention, where no washing step is applied, hydrophobic uncharged aromatic amino acids are selected from tyrosine, phenylalanine, tryptophan and mixtures thereof. Where a washing step is applied, hydrophobic uncharged aromatic amino acids are selected from, phenylalanine, tryptophan and mixtures thereof.

Polar uncharged amino acids are selected from serine, glutamine, threonine, asparagine, methionine and mixtures thereof.

Positively charged amino acids are selected from lysine, histidine and mixtures thereof.

Negatively charged amino acids are selected from aspartate, glutamic acid and mixtures thereof.

Thus, in the method of the invention, where no washing step is applied, the N-acetyl amino acid may be selected from the group consisting of N-acetyl glycine, N-acetyl alanine, N-acetyl proline, N-acetyl leucine, N-acetyl isoleucine, N-acetyl valine, N-acetyl tyrosine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof, preferably N-acetyl alanine, N-acetyl proline, N-acetyl leucine, N-acetyl isoleucine, N-acetyl valine, N-acetyl tyrosine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

In the method of the invention, where a washing step is applied, the N-acetyl amino acid may be selected from the group consisting of N-acetyl glycine, N-acetyl alanine, N-acetyl proline, N-acetyl leucine, N-acetyl isoleucine, N-acetyl valine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof, preferably N-acetyl alanine, N-acetyl proline, N-acetyl leucine, N-acetyl isoleucine, N-acetyl valine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

The N-acetyl amino acid may be used in the free acid form or in the form of salts such as the sodium, potassium, and ammonium salts, or the lower alkanolamine salts (such as mono-, di- and triethanolamine salts and mono-, di- and triisopropanolamine salts). Mixtures of any of the above-described forms may also be suitable.

Preferably the N-acetyl amino acid is used at a level ranging from 0.1 to 6%, more preferably from 0.5 to 3% and most preferably from 1 to 2.5% (by weight based on the total weight of the composition). The concentration will be affected in part by the solubility of the parent amino acid and should be chosen accordingly.

The aqueous treatment composition is used at natural pH.

The Aqueous Treatment Composition

Preferably, the aqueous treatment composition comprises at least 20 wt %, more preferably 80 wt % and most preferably at least 99 wt % water, by total weight of the composition.

The aqueous treatment composition may be applied before, during or after a washing process. Preferably, the composition of the invention may be applied to the hair as part of a daily wash and care or treatment regime.

The aqueous treatment composition may be a leave-on or a rinse off composition.

Rinse off aqueous treatment compositions for use in the invention are typically left on hair for 1 to 2 minutes before being rinsed off.

Leave-on aqueous treatment compositions for use in the invention are typically applied to the hair and left on the hair for more than 10 minutes.

The aqueous treatment composition of the present invention is preferably selected from a shampoo, a conditioner, a mask and a leave-on product. A conditioner composition comprises a conditioning agent.

Hair masks for use in the present invention are treatments that are typically left on the hair for 3 to 10 minutes, preferably from 3 to 5 minutes, more preferably 4 to 5 minutes, before being rinsed off.

Conditioner Base

An aqueous treatment composition for use in the method of the invention may suitably include a conditioning gel phase, which may be generally characterized as a gel (Lβ) surfactant mesophase consisting of surfactant bilayers. Such a conditioning gel phase may be formed from a cationic surfactant, a high melting point fatty alcohol and an aqueous carrier. Typically, these components are heated to form a mixture, which is cooled under shear to room temperature. The mixture undergoes a number of phase transitions during cooling, normally resulting in a gel (L$_β$) surfactant mesophase consisting of surfactant bilayers.

Examples of suitable cationic surfactants which are useful for forming the conditioning gel phase include quaternary ammonium cationic surfactants corresponding to the following general formula:

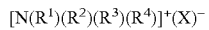

in which $R^1$, $R^2$, $R^3$, and $R^4$ are each independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halide, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Specific examples of such quaternary ammonium cationic surfactants of the above general formula are cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by other halide (e.g., bromide), acetate, citrate, lactate, glycolate, phosphate nitrate, sulphate, or alkylsulphate.

In a preferred class of cationic surfactant of the above general formula, $R^1$ is a $C_{16}$ to $C_{22}$ saturated or unsaturated, preferably saturated, alkyl chain and $R^2$, $R^3$ and $R^4$ are each independently selected from $CH_3$ and $CH_2CH_2OH$, preferably CH₃. Specific examples of such preferred quaternary ammonium cationic surfactants for use in forming the conditioning gel phase are cetyltrimethylammonium chloride (CTAC), behenyltrimethylammonium chloride (BTAC) and mixtures thereof.

Mixtures of any of the above-described cationic surfactants may also be suitable.

The level of cationic surfactant suitably ranges from 0.1 to 10%, preferably from 0.2 to 5% and more preferably from 0.25 to 4% (by weight based on the total weight of the composition).

By "high melting point" in the context of this invention is generally meant a melting point of 25° C. or higher. Generally, the melting point ranges from 25° C. up to 90° C., preferably from 40° C. up to 70° C. and more preferably from 50° C. up to about 65° C.

The high melting point fatty alcohol can be used as a single compound or as a blend or mixture of at least two high melting point fatty alcohols. When a blend or mixture of fatty alcohols is used, the melting point means the melting point of the blend or mixture.

Suitable fatty alcohols of this type have the general formula R—OH, where R is an aliphatic carbon chain. Preferably R is a saturated aliphatic carbon chain comprising from 8 to 30 carbon atoms, more preferably from 14 to 30 carbon atoms and most preferably from 16 to 22 carbon atoms.

R can contain, in addition to carbon and hydrogen atoms, ether linkages, and other groups such as amino groups.

Most preferably, the fatty alcohol has the general formula $CH_3(CH_2)_n OH$, where n is an integer from 7 to 29, preferably from 15 to 21.

Specific examples of suitable fatty alcohols are cetyl alcohol, stearyl alcohol, behenyl alcohol, and mixtures thereof. Cetyl alcohol, stearyl alcohol and mixtures thereof are particularly preferred.

Mixtures of any of the above-described fatty alcohols may also be suitable.

The level of fatty alcohol suitably ranges from 0.01 to 10%, preferably from 0.1 to 8%, more preferably from 0.2 to 7% and most preferably from 0.3 to 6% (by weight based on the total weight of the composition).

The weight ratio of cationic surfactant to fatty alcohol is suitably from 1:1 to 1:10, preferably from 1:1.5 to 1:8, optimally from 1:2 to 1:5.

Optional Ingredients

An aqueous treatment composition for use in step (i) of the method of the invention may also incorporate other optional ingredients to enhance performance and/or consumer acceptability. Suitable optional ingredients include: preservatives, colouring agents, chelating agents, antioxidants, fragrances, antimicrobials, antidandruff agents, cationic conditioning polymers, styling ingredients, sunscreens, proteins and hydrolysed proteins.

The method of the invention is a method of repairing oxidatively-treated hair.

Step (i)—the Soak Step

In step (i) of the method of the invention, the washed hair is soaked in the aqueous treatment composition. Generally, any application amount of aqueous treatment composition that covers the hair to be treated suffices. Lesser amounts may be used, for example, if only a section of hair or just the hair tips are to be treated. The aqueous treatment composition is preferably uniformly delivered, for example by working it from the root end to the tip end of the hair.

Preferably, the hair is soaked in the aqueous treatment composition at a temperature from 15 to 40° C., and more preferably at a temperature from 20 to 30° C.

Preferably, the hair is soaked in the aqueous treatment composition for a period ranging from 1 to 60 minutes, more preferably from 3 to 45 minutes.

Step (ii)—the Rinse Step

In step (ii) of the method of the invention, the dry hair is rinsed in water. The hair may be submerged, or held under flowing water, preferably the hair is held under flowing water. The hair may be agitated during rinsing. Preferably the water is warm.

Step (iii)—a Post-Wash Step

In one embodiment of the invention, the hair is washed following rinsing of the aqueous treatment composition. The hair is washed with a composition that comprises a cleansing surfactant, preferably a shampoo.

The Optional Drying Step

The hair may be dried naturally by exposure to air, by use of a heated hair drying appliance, by rubbing with a water-absorbent article, or by a combination of any of these methods. Preferably, the hair is dried following rinsing the aqueous treatment composition from the hair.

The Hair

The method of this invention is applied to oxidatively-treated hair.

As used herein, the term "oxidatively-treated hair" means hair which has been subjected to any treatment comprising at least one step of contacting the hair with at least one oxidizing composition. Examples of oxidative treatments for human hair are bleaching, dyeing or perming.

As used herein, the term "oxidizing composition" means a composition comprising at least one oxidizing agent suitable for use on hair, such as hydrogen peroxide, potassium, sodium or ammonium salts of perborate, percarbonate, persulfate and percarbamide, and mixtures thereof. Examples of such compositions are oxidative dye compositions and bleaching compositions.

The invention is further illustrated with reference to the following, non-limiting Examples.

EXAMPLES

In the Examples, all ingredients are expressed by weight percent of the total formulation, and as level of active ingredient. Comparative Examples (not according to the invention) are indicated by a letter; Examples according to the invention are indicated by a number.

Hair that has been damaged has internal protein with a reduced denaturation temperature compared to that of virgin hair. The reduction in denaturation temperature is attributed to a degradation of the internal hair cortex proteins.

Hair damage can be measured in different ways. This invention focusses on the structural integrity of hair cortex proteins, as can be determined by Differential Scanning Calorimetry.

Method of Bleaching Hair

Hair was bleached for 30 min with Platine Precision White Compact Lightening Powder (L'Oreal Professionnel Paris, Paris, France) mixed with 9% cream peroxide, 30 'vol' (Excel GS Ltd, UK) (60 g of powder mixed with 120 g cream peroxide). Hair was then rinsed with water for 2 minutes. This procedure was repeated on the same hair to produce twice bleached hair.

In the following examples, compositions A-C are comparative examples and 1-6 are in accordance with the invention. The compositions are 1% aqueous solutions of various N-Acetyl amino acids, prepared by adding the N-acetyl amino acid to water with stirring.

Example 1: Treatment of Hair with N-Acetyl Alanine, N-Acetyl Arginine, N-Acetyl-Cysteine, N-Acetyl Glutamic Acid, N-Acetyl Glutamine, N-Acetyl Proline, N-Acetyl Serine, N-Acetyl Tyrosine, N-Acetyl Tryptophan, N-Acetyl Methionine, N-Acetyl Histidine and N-Acetyl Leucine In the following experiments, Control 1 and 2 were from two different batches of twice bleached hair. They were dialysed with water before being used.

Experiment 1—Step (i)—Soak

Twice bleached dark brown European hair was soaked for 30 minutes in 1% aqueous solutions of various N-Acetyl amino acids. The hair was then removed from the solution. Clippings from a few fibres were then taken and the denaturation temperature (Td) was measured using DSC. The results are given in Table 1 below.

N-acetyl alanine, N-acetyl arginine, N-acetyl-cysteine, N-acetyl glutamic acid, N-acetyl glutamine, N-acetyl proline, N-acetyl serine and N-acetyl tyrosine were tested against Control 1.

N-acetyl tryptophan, N-acetyl methionine, N-acetyl histidine and N-acetyl leucine were tested against Control 2.

TABLE 1

Denaturation Temperature (Td) of hair treated with compositions 1% aqueous solutions of N-acetyl alanine, N-acetyl arginine, N-acetyl-cysteine, N-acetyl glutamic acid, N-acetyl glutamine, N-acetyl proline, N-acetyl serine, N-acetyl tyrosine, N-acetyl tryptophan, N-acetyl methionine, N-acetyl histidine and N-acetyl leucine.

| Active | Denaturation Temperature Td (n = 3) | Difference from control |
| --- | --- | --- |
| Control 1 | 148.60 | n/a |
| N-Acetyl Arginine | 148.57 | −0.03 |
| N-Acetyl Cysteine | 149.27 | 0.67 |
| N-Acetyl Alanine | 156.00 | 7.4 |
| N-Acetyl Glutamic acid | 154.69 | 6.09 |
| N-Acetyl Glutamine | 155.15 | 6.55 |
| N-Acetyl Proline | 154.46 | 5.86 |
| N-Acetyl Serine | 156.25 | 7.65 |
| N-Acetyl Tyrosine | 155.00 | 6.4 |
| Control 2 | 145.57 | n/a |
| N-Acetyl Tryptophan | 151.68 | 6.11 |
| N-Acetyl Methionine | 153.36 | 7.79 |
| N-Acetyl Histidine | 148.08 | 2.51 |
| N-Acetyl Leucine | 149.48 | 3.91 |

Table 1 shows that hair treated with N-Acetyl amino acids, other than N-Acetyl Arginine and N-Acetyl Cysteine, has substantially higher Td than hair treated with the control composition. The increased Td is consistent with reduced damage as a result of repair to the internal proteins of the bleached hair. These results were used as a baseline for the method of the invention in the following experiments.

Experiment 2—Steps (ii)—Rinse

The effect of a subsequent rinse step was determined. Only N-acetyl amino acids that showed increases that were statistically significant in the previous experiment were looked at; these were designated Compositions 1-6.

The switches from experiment 1 were rinsed in running water for 30 seconds. Clippings from a few fibres were used to measure denaturation temperature Td using DSC and these are given below.

TABLE 2

Denaturation Temperature (Td) of hair treated with Compositions 1-6 and rinsed in accordance with the invention and Comparative Composition A

| | Actives | Td (n = 3) | Difference from control |
| --- | --- | --- | --- |
| A | Control 1 | 148.78 | |
| 1 | N-Acetyl Alanine | 152.99 | 4.2 |
| 2 | N-Acetyl Glutamic acid | 152.67 | 3.89 |
| 3 | N-Acetyl Glutamine | 150.75 | 1.97 |
| 4 | N-Acetyl Proline | 150.95 | 2.16 |
| 5 | N-Acetyl Serine | 151.80 | 3.02 |
| 6 | N-Acetyl Tyrosine | 151.63 | 2.85 |
| 7 | Control 2 | 146.12 | n/a |
| 8 | N-Acetyl Tryptophan | 150.43 | 4.31 |
| 9 | N-Acetyl Methionine | 149.97 | 3.85 |
| 10 | N-Acetyl Histidine | 147.76 | 1.64 |
| 11 | N-Acetyl Leucine | 150.03 | 3.91 |

The increases in Td are statistically significant (>99%).

Surprisingly, even after a rinse, hair treated with the N-Acetyl amino acids in accordance with the invention, retain significant Td increases, which shows that the treatment is durable to rinsing.

Experiment 3—Step (iii)—Wash

The rinsed switches of experiment 2 were washed with base wash (14% SLES solution) and DSC performed.

Hair was washed with a cleansing shampoo using the following method:—

The hair fibres were held under running water for 30 seconds, shampoo applied at a dose of 0.1 ml of shampoo per 1 g of hair and rubbed into the hair for 30 seconds. Excess lather was removed by holding under running water for 30 seconds and the shampoo stage repeated. The hair was rinsed under running water for 1 minute.

The results are shown in Table 3 below.

TABLE 3

Denaturation Temperature (Td) of Examples 1-6 in accordance with the invention and Comparative Example A

| | Actives | Td (n = 3) | Difference from control |
| --- | --- | --- | --- |
| A | Control (DB) | 148.36 | |
| 1 | N-Acetyl Alanine | 151.11 | 2.76 |
| 2 | N-Acetyl Glutamic acid | 151.26 | 2.90 |
| 3 | N-Acetyl Glutamine | 150.85 | 2.50 |
| 4 | N-Acetyl Proline | 149.43 | 1.08 |
| 6 | N-Acetyl Tyrosine | 148.04 | −0.32 |
| 7 | Control 2 | 145.72 | n/a |
| 8 | N-Acetyl Tryptophan | 150.43 | 4.71 |
| 9 | N-Acetyl Methionine | 151.14 | 5.42 |
| 10 | N-Acetyl Histidine | 147.65 | 1.93 |
| 11 | N-Acetyl Leucine | 150.70 | 4.98 |

All increases are significant to >98%;

The table above shows that with the exception of N-acetyl Tyrosine, hair treated with N-acetyl amino acids have a durable Td increase, which persists even after a further wash.

Thus many N-Acetyl amino acids have the potential to show to various extents long lasting damage care benefits on oxidatively damaged hair that can survive a rinse and a wash.

The invention claimed is:

1. A method of repairing oxidatively-treated hair, the method consisting of:
    (i) soaking hair in an aqueous treatment composition;

(ii) rinsing the hair of step (i);
(iii) optionally washing the hair of step (ii); and
(iv) optionally drying the hair after step (ii) and/or after step (iii)
wherein the aqueous treatment composition comprises 0.1 to 6 wt % N-acetyl amino acid, based on the total weight of the composition,
wherein the N-acetyl amino acid is selected from the group consisting of N-acetyl glycine, N-acetyl alanine, N-acetyl proline, N-acetyl leucine, N-acetyl isoleucine, N-acetyl valine, N-acetyl tyrosine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

2. The method of claim 1, wherein the rinsed hair is washed, and
wherein the N-acetyl amino acid is selected from the group consisting of N-acetyl glycine, N-acetyl alanine, N-acetyl proline, N-acetyl leucine, N-acetyl isoleucine, N-acetyl valine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

3. The method of claim 1, wherein the rinsed hair is dried.

4. The method of claim 1, wherein the N-acetyl amino acid is used in the free acid form.

5. The method of claim 1, wherein the hair is soaked in the aqueous treatment composition at a temperature of from 15° C. to 40° C.; for a period of 3 min to 45 min.

6. The method of claim 1, wherein the aqueous treatment composition comprises an aqueous continuous phase.

7. The method of claim 1, wherein the aqueous treatment composition is a hair conditioner comprising a conditioning agent.

8. The method of claim 1, wherein the aqueous treatment composition is a shampoo, a conditioner, a mask or a leave-on product.

9. A method of repairing oxidatively-treated hair, the method comprising:
(i) soaking hair in an aqueous treatment composition; and
(ii) rinsing the hair of step (i);
wherein the aqueous treatment composition consists of:
(a) 0.1 to 6 wt % N-acetyl amino acid, based on the total weight of the composition,
(b) a conditioning gel phase, formed from a cationic surfactant, a high melting point fatty alcohol and an aqueous carrier;
(c) optionally one or more ingredients selected from preservatives, colouring agents, chelating agents, antioxidants, fragrances, antimicrobials, antidandruff agents, cationic conditioning polymers, styling ingredients, sunscreens, proteins and hydrolysed proteins;
(d) optionally an organic solvent; and
(e) water
wherein the N-acetyl amino acid is selected from the group consisting of N-acetyl glycine, N-acetyl alanine, N-acetyl proline, N-acetyl leucine, N-acetyl isoleucine, N-acetyl valine, N-acetyl tyrosine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

10. The method of claim 9, which further comprises a step (iii), sequential to step (ii), comprising washing the hair of step (ii), and
wherein the N-acetyl amino acid is selected from the group consisting of N-acetyl glycine, N-acetyl alanine, N-acetyl proline, N-acetyl leucine, N-acetyl isoleucine, N-acetyl valine, N-acetyl phenylalanine, N-acetyl tryptophan, N-acetyl serine, N-acetyl glutamine, N-acetyl threonine, N-acetyl asparagine, N-acetyl methionine, N-acetyl lysine, N-acetyl histidine and mixtures thereof.

11. The method of claim 9, which further comprises a drying step.

12. The method of claim 11, wherein the rinsed hair is dried.

13. The method of claim 9, wherein the N-acetyl amino acid is used in the free acid form.

14. The method of claim 9, wherein the hair is soaked in the aqueous treatment composition at a temperature of from 15° C. to 40° C.

15. The method of claim 9, wherein the hair is soaked in the aqueous treatment composition for a period ranging from 3 minutes to 45 minutes.

16. The method of claim 9, wherein the aqueous treatment composition comprises an aqueous continuous phase.

17. The method of claim 9, wherein the cationic surfactant comprises a quaternary ammonium cationic surfactant having the general formula:

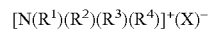

wherein $R^1$, $R^2$, $R^3$, and $R^4$ are each independently selected from:
(a) an aliphatic group of from 1 to 22 carbon atoms, or
(b) an aromatic, alkoxy, polyoxyalkylene, alkylamido, hydroxyalkyl, aryl or alkylaryl group having up to 22 carbon atoms; and X is a salt-forming anion such as those selected from halide, acetate, citrate, lactate, glycolate, phosphate nitrate, sulphate, and alkylsulphate radicals.

18. The method of claim 17, wherein the quaternary ammonium cationic surfactant is selected from the group consisting of cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, dipalmitoylethyldimethylammonium chloride, and PEG-2 oleylammonium chloride; and salts thereof, wherein the chloride is replaced by other halide, acetate, citrate, lactate, glycolate, phosphate nitrate, sulphate, or an alkylsulphate.

19. The method of claim 9, wherein the high melting point fatty alcohol has the general formula $CH_3(CH_2)_nOH$; where n is an integer from 7 to 29.

20. The method of claim 19, wherein the high melting point fatty alcohol is selected from the group consisting of cetyl alcohol, stearyl alcohol, behenyl alcohol, and mixtures thereof.

* * * * *